United States Patent
Deshpande et al.

(10) Patent No.: US 6,384,215 B1
(45) Date of Patent: May 7, 2002

(54) PREPARATION OF NEW INTERMEDIATES AND THEIR USE IN MANUFACTURING OF CEPHALOSPORIN COMPOUNDS

(75) Inventors: Pandurang Balwant Deshpande; Parven Kumar Luthra, both of Tamilnadu (IN)

(73) Assignee: Orchid Chemicals & Pharmaceuticals Ltd., Tamil Nadu (IN)

( * ) Notice: Subject to any disclaimer, the term of this patent is extended or adjusted under 35 U.S.C. 154(b) by 0 days.

(21) Appl. No.: 09/875,043

(22) Filed: Jun. 7, 2001

(51) Int. Cl.$^7$ .................. C07D 271/08; C07D 501/04

(52) U.S. Cl. ........................ 540/227; 548/144

(58) Field of Search ........................... 548/144; 540/227

(56) References Cited

PUBLICATIONS

Salama Egyptian J Chem 24(1–3) 47–51 1982.*

\* cited by examiner

*Primary Examiner*—Robert Gerstl
(74) *Attorney, Agent, or Firm*—Burns, Doane, Swecker & Mathis, L.L.P.

(57) ABSTRACT

The present invention provides new thioester derivatives of 4-halogeno-2-methoxyimino-3-oxo-butyric acid of the general formula (I), also, the invention provides a method by which the said thioester derivatives can be prepared by reacting 4-halogeno-2-methoxyimino-3-oxo-butyric acid of the general formula (II) with 2-mercapto-5-substituted-1,3, 4-oxadiazoles of the general formula (III) in a solvent, in the presence of DMF/POCl$_3$ and in presence of an organic base and if desired the so obtained thioester derivatives so obtained are reacted with 7-amino-cephem carboxylic acids of the general formula (V) to produce condensed products which are insitu reacted with thiourea to get cephalosporin antibiotic compounds having the general formula (VI).

12 Claims, No Drawings

PREPARATION OF NEW INTERMEDIATES AND THEIR USE IN MANUFACTURING OF CEPHALOSPORIN COMPOUNDS

FIELD OF INVENTION

The present invention relates to novel thioester derivatives of the general formula (I) prepared by the reaction of 4-halogeno-2-methoxyimino-3-oxo-butyric acid (II) with 5-substituted-1,3,4-oxadiazole-2-thiol of formula (III). The invention also discloses the use of the new intermediate (I) for the preparation of cephalosporanic antibiotics (VI) in excellent yields and purity.

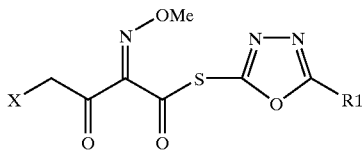

(I)

wherein

X represents halogen (Cl,Br and I)

$R_1$ represents $C_1$–$C_4$ alkyl or phenyl

BACKGROUND OF THE INVENTION

Acid chlorides, anhydrides, esters, amide etc. are reported in the chemical literature for activation of carboxylic acid of formula (IV). Activation in the form of acid chloride required protection and deprotection of $NH_2$ group.

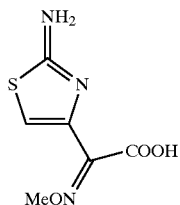

(IV)

Activation of 2-(2-aminothiazol-4-yl)-2-methoxyiminoacetic acid (IV) by $SO_2Cl_2$/DMF is reported in U.S. Pat. No. 5,856,502 and activation of $SOCl_2$/DMF is reported in U.S. Pat. No. 5,037,988. These processes suffers with the limitation of poor by moderate yields along with the use of solvents like benzene and stringent conditions required for carrying out the reactions at commercial scale.

In U.S. Pat. Nos. 4,576,749 and 4,548,748 the acid of formula (IV) have also been activated by reacting with 1-hydroxybenzotriazole (HOBT) or 2-mercaptobenzothiazole (MBT) in the presence of dicyclohexylcarbodiimide (DCC) to produce reactive ester of the acid (IV) which reacted to cephem moiety to prepare cephem antibiotics, but the processes are time consuming and with low yields, hence not suitable.

U.S. Pat. No. 4,767,852 discloses a process for production of cephems by acylating 7-amino-3-cephem-4-carboxylic acid with 2-mercaptobenzothiazolyl-(Z)-2-(2-aminothiazol-4-yl)-2-methoxyiminoacetate (MAEM). Similarly, U.S. Pat. No. 5,026,843 disclosed a process for preparing ceftriaxone disodium hemiheptahydrate by acylation of 7-amino-3-[[(2,5-dihydro-6-hydroxy-2-methyl-5-oxo-1,2,4-triazin-3yl)thio]methyl]3-cephem-4-carboxylic acid (ACT) by using MAEM as acylating agents in good yield and quality. Thus MAEM has become the standard acylating agent for the preparation of cephalosporins having an oximino group and a 2-aminothiazolyl group in 7-position of cephem compounds.

However, the synthesis of MAEM from 2-(2-aminothiazol-4-yl)-2-methoxyiminoacetic acid (IV) and 2,2'-dithio-bis-benzothiazole involves use of costly condensing agent triphenylphosphine (TPP). Moreover, during condensation of MAEM with 7-amino-3-cephem-4-carboxylic acid compound (V), a toxic compound MBT is also produced as a byproduct, see e.g., Chemical Abstracts, 111, 19243$_p$ (1989) which is difficult to remove completely.

Thus it is evident that the procedures described in the prior art for preparation of these antibiotics are complex, involving protection, deprotection and are associated with toxic byproduct generation. Hence there is a need to develop new acylating agents which are capable of transferring the 2-aminothiazolyl moiety to cephem compounds of formula (V) in good yield but without producing this toxic byproduct. On the similar lines, a new thioester was reported by D. G. Walker, Tet. Lett. 1990, 31,6481 to acylate the cephem moiety to get cefepime sulfate but yields obtained by using this thioester were in the range of 54–73% which cannot be considered as good yield to operate a process at commercial scale. The use of this thioester was reported in the Tet. Lett. 1990, 31, 6481 only for cefepime and not for other cephalosporins. This thioester was exploited in U.S. Pat. No. 5,869,649 for making three other important cephem antibiotics.

Synthesis of 4-halogeno-2-methoxyimino-3-oxo-butyric acid is reported in Patent No. EP 0 030 294 and a large number of references are available in the patent literature disclosing the use of 4-halogeno-2-methoxyimino-3-oxobutyric acid represented by formula (II) as the starting material. EP 0 030 294 and WO 00 0063214 discloses the condensation of the 4-halogeno-2-methoxyimino-3-oxobutyric acid represented by formula (II) with cephem carboxylic acids by using $PCl_5$ Another EP Patent No. 0 842 937 discloses the formation of amide bond with cephem moiety by reacting with the thioester derivative prepared by using 2,2'-dithio-bis-benzothiazole. The preparation of this active thioester involves use of same costly condensing agent triphenylphosphine (TPP) which has been mentioned earlier in the text. Broadly the use of 4-halogeno-2-methoxyimino-3-oxo-butyric acid represented by formula (II) also suffer with almost in same disadvantages which are commonly prevalent for 2-(2-aminothiazol-4-yl)-2-methoxyiminoacetic acid (IV).

OBJECTS OF THE INVENTION

The primary objective of the invention is to provide new reactive thioester derivatives of 4-halogeno-2-methoxyimino-3-oxo-butyric acid of the general formula (I), which would be suitable for being used in the manufacture of cephalosporin antibiotics and would not be associated with the complexities mentioned above.

Another objective of the present invention is to provide a process for the preparation of above mentioned new thioesters (I) in good yields.

One more objective of the present invention is to provide a process for the preparation of cephalosporin antibiotics of the general formula (VI) from the said novel thioester derivatives.

Another objective of the present invention is to provide a process for the preparation of cephalosporin antibiotics e.g., cefotaxime, ceftriaxone, cefetamet, ceftiofur, cefpodoxime etc. which comprises condensation of new reactive derivatives (I) with cephem compounds (V) and in situ cyclisation with thiourea to obtain targeted antibiotics(VI) in excellent yields and purity.

Still another objective of the present invention is to produce cephalosporin antibiotics that are highly pure and free from toxic byproducts.

SUMMARY OF THE INVENTION

The present invention provides novel thioester derivatives of 4-halogeno-2-methoxyimino-3-oxo-butyric acid of the general formula (I) also, the invention provides a method by which the said thioester derivatives can be prepared by reacting of 4-halogeno-2-methoxyimino-3-oxo-butyric acid of the general formula (II) with 2-mercapto-5-substituted-1,3,4-oxadiazole of the general formula (III) (preparation of III, J. Am. Chem. Soc., 1955, 77, 400) by activating with DMF/POCl$_3$ in presence of an organic base in a solvent. The so obtained thioester derivatives are reacted with 7-aminocephem carboxylic acids of the general formula (V) to produce cephalosporin antibiotic compounds having the general formula (VI).

DETAILED DESCRIPTION OF THE INVENTION

The present invention provides new thioesters of 4-halogeno-2-methoxyimino-3-oxo-butyric acid of general formula (I). The synthesis of compound (I) is achieved by preparing activated complex of 4-halogeno-2-methoxyimino-3-oxo-butyric acid (II) with DMF-POCl$_3$ followed by the reaction with thio-oxadiazoles of the general formula (III) in organic solvent in presence of an organic base at the temperature between −30° C. and +20° C. The reactive active ester is obtained quantitative yields (95–99%).

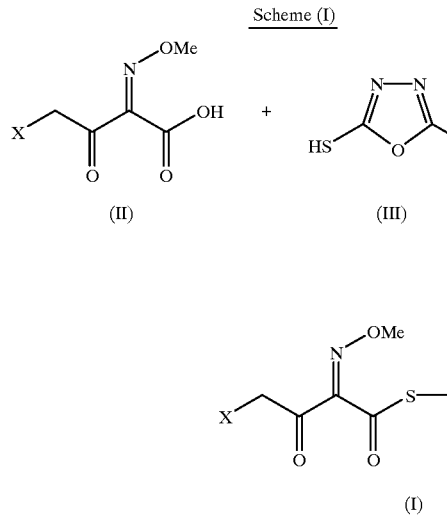

wherein
  X represents halogen
  R$_1$ represents C$_1$–C$_4$ alkyl or phenyl

The reactive thioester were characterized by NMR, IR and Mass spectra.

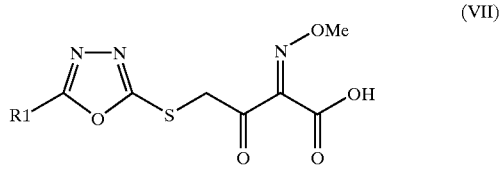

A major side product (VII) which is formed during this reaction has also been controlled in the process. Surprisingly this side reaction has never been mentioned in the literature.

In an embodiment, in the compound of formula (I), X is chloro, bromo or iodo.

In another embodiment the organic solvent is selected from the group comprising dichloromethane, tetrahydrofuran, dioxane, N,N-dimethylformamide, acetonitrile and mixtures thereof.

In still another embodiment the organic base is selected from the group comprising triethylamine, diethylamine, tributylamine, pyridine, N-alkylanilines, and mixtures thereof.

The compound (I) so obtained is reacted with 7-amino cephem carboxylic acid of general formula (V) in two different methods and both the methods lead to same product with comparable yields and purity.

Using above mentioned thioester the cephalosporin antibiotics obtained are of high purity (90–99%). The method gives an excellent yield (70–95%) of cephalosporin without necessitating the protection of the amino group of the acylating agents, and the toxic byproduct 2-mercaptobenzothiazole is not produced.

The cephalosporin antibiotic were synthesized by following two methods:

Method -I

The reactive thioester (I) was reacted with 7-aminocephem compound (V)

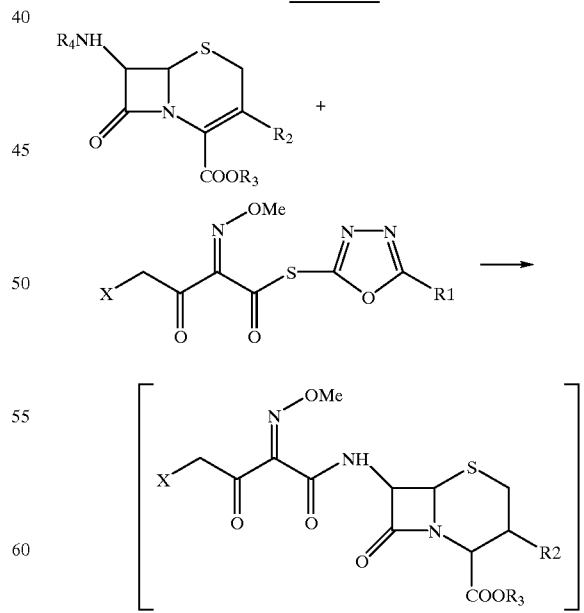

-continued

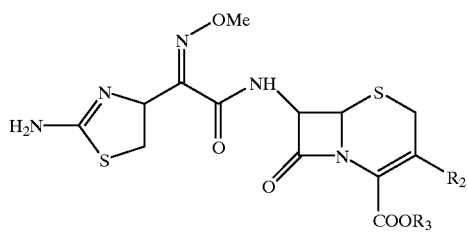

wherein

R₁ represents $C_1$–$C_4$ alkyl or phenyl

R₂ represents H, $CH_3$, $CH_2OCH_3$, $CH_2OCOCH_3$,

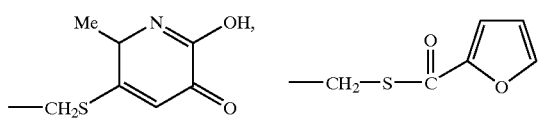

or a standard cephalosporin substituent

R₃ is hydrogen, salt or carboxylic protecting group.

R₄ is hydrogen or silyl.

In organic solvent in the presence of base to obtained condensed product, which was not isolated and is directly cyclised with thiourea in mixture of water and a polar organic solvent like tetrahydrofuran, dimethylformamide, dioxane, alcohol to obtain desired cephalosporanic antibiotics of very good purity and excellent yields.

Method -II

In this approach, starting from active ester of formula (I) final product was prepared in one pot reaction. The process comprises cyclization of active ester in the first step and in same reactor addition of amino cephem compound in mixture of water and a polar organic solvent like tetrahydrofuran, dimethylformamide, dioxane, alcohols to obtain desired cephalosporanic antibiotics of equally good purity and yields as compared to first approach. This approach provides a simple, cheap and commercially viable method without the necessity of isolating thioester and without producing any toxic byproduct namely 2-mercaptobenzothiazole.

The substituent R₂ in cephem compound (V) and (VI) represents hydrogen, methyl, acetyloxymethyl, methoxymethyl, 2,5-dihydro-6-hydroxy-2-methyl-5-oxo-1,2,4-triazine-3-thiol, furanyl-2-carbonyl thiol or a standard cephalosporin substituents.

R₃ in cephem compound (V) and (VI) represents hydrogen, salt or a ester group which can be easily removed e.g., p-methoxybenzyl, p-nitrobenzyl, diphenylmethyl, phenacyl, trimethylsilyl etc.

In an embodiment of the present invention the organic base may be selected from the group consisting of triethylamine, N-methylmorpholine, pyridine, N-methylanilines, 1,5-diazabicyclo[4.3.0] non-5-ene, 1,4-diazabicyclo[2.2.2]octane, 4-dimethylaminopyridine, and mixtures thereof.

Many other beneficial results can be obtained by applying disclosed invention in a different manner or by modifying the invention with the scope of disclosure. However, since the major characteristic feature of the present invention resides in the use of novel reactive thioester derivatives of 4-bromo-2-methoxyimino-3-oxo-butyric acid of the general formula (I) in preparing the cephalosporin antibiotics, the technical scope of the present invention should not be limited to the following examples. The following examples are provided to illustrate but not to limit the claimed invention.

EXPERIMENTAL

Example 1

Synthesis of 2-mercapto-5-phenyl-1,3,4-oxadiazolyl-(Z)-4-bromo-2-methoxyimino-3-oxo-butyrate (I).

Phosphorus oxy chloride (25.6 g) was added slowly to N,N-dimethyl formamide (12.2 g) at 0 to –5° C. Stirred for 30 minutes. Acetonitrile (200 ml) was added followed by 4-bromo-2-methoxyimino-3-oxo-butyric acid (25.0 g) and 5-phenyl-1,3,4-oxadiazole-2-thiol (19.8 g). Pyridine (44.1 ml) was slowly added to the flask at –10° C. The progress of the reaction was monitored by HPLC. After the disappearance of the starting material, the reaction mass was poured into ice-water, white colored solid separated out which was filtered and washed with water. Dried under vacuum to obtain 40.8 gm of thioester with HPLC purity (96.0–98.0%).

Melting point: 139–140° C.

$^1$HNMR (DMSO-$d_6$): δ4.1 (3H,s,N—O$\underline{CH_3}$), 4.3(2H,s,Br $\underline{CH_2}$CO) 7.6–7.9(5H, m, —$C_6H_5$)

$^{13}$C-NMR(CDCl₃): δ30.2, 65.8, 121.3, 127.7, 129.7, 134.1, 147.5, 147.8, 156.3, 160.2, 186.1.

Example 2

3-Acetyloxymethyl-7-[(Z)-(2-aminothiazolyl-4-yl)-2-(methoxyimino)acetamido]-3-cephem-4-carboxylic acid (Cefotaxime acid).

Method -I

A mixture of THF (250 ml) and water (150 ml) and N,N-dimethylacetamide (25.0 ml) was stirred under inert atmosphere. At 0°–5° C., 7-aminocephalosporanic acid (25.0 g) and 2-mercapto-5-phenyl-1,3,4-oxadiazolyl-(Z)-4-bromo-2-methoxyimino-3-oxo-butyrate (46.0 g) were added. Triethylamine (20.4 g) was slowly added to reaction by maintaining pH 7.0 to 8.0. The reaction was checked by HPLC. After 6–8 hrs., the reaction mixture was extracted by methylene chloride(200×3). The aqueous layer is subjected for charcoal treatment. Thiourea (18.4 g) and sodium acetate (4.2 g) were added to the filtered aqueous layer and stirred for 1.0 hr to get the cefotaxime which was isolated with subsequent acidification of the aqueous layer with dil. HCl at 10° C. to pH 3.0. The solid separated was filtered, washed with water and ethylacetate and then dried under vacuum at 40–45° C. to get Cefotaxime, 40.9 g (yield 98%).

HPLC (purity)=98–99%

Method -II

2-Mercapto-5-phenyl-1,3,4-oxadiazolyl-(Z)-4-bromo-2-methoxyimino-3-oxo-butyrate (46.0 g) was taken in a mixture of tetrahydrofuran (250 ml) and water (150 ml). The solution was cooled to 10° C. and the thiourea (20.47 g) and sodium acetate (4.32 g) were added. The reaction mixture was stirred for 1.0 hr. 7-amino cephalosporanic acid (25.0 g) was added followed by slow addition of triethylamine (20.4 g) the progress of the reaction was monitored by HPLC. The reaction was completed in 6–8 hr. The reaction mixture was extracted with dichloromethane (3×200 ml). The aqueous layer was acidified with dil. HCl to obtain cefotaxime, 38.0 g.

Example 3

7-[[(Z)-2-(2-Aminothiazol-4-yl)2-methoxyimino] acetamido]-3-[[(2,5-dihydro-6-hydroxy-2-methyl-5-oxo-1, 2,4-triazin-3-yl)thio]methyl]-3-cephem-4-carboxylic acid disodium hemiheptahydrate (Ceftriaxone sodium).

Method -I

7-Amino-3-[[(2,5-dihydro-6-hydroxy-2-methyl-5-oxo-1, 2,4-triazin-3yl)thio]methyl]3-cephem-4-carboxylic acid (20.0 g) and 2-mercapto-5-phenyl-1,3,$^4$-oxadiazolyl-(Z)-4-bromo-2-methoxyimino-3-oxo-butyrate (27.2 g) were suspended in a mixture of THF (180 ml), H$_2$O (80 ml) and DMAc (30 ml) maintained at 0–1° C. under stirring. Triethylamine (11.9 ml) was added in 2–3 hours at 5° C. maintaining the pH 7.5–8.5. The reaction progress was monitored by HPLC. After the reaction was completed, the mixture was extracted with dichloromethane (3×100 ml). The aq. layer was separated and treated with charcoal (0.2 g). Thiourea (10.9 g) is added to the solution and stirred for 1.0 hr. till cyclisation is over. A solution of sodium-2-ethylhexanoate (30.5 g) in acetone was added at 10–15° C. and stirred for 1.5 hours (400 ml) of acetone was added in 1 hour at 10–15° C. to complete the crystallization. The product was filtered under N$_2$ atmosphere and wet cake was dissolved in mixture of water and acetone (1:2), and cooled to −10° C. Colored impurities were separated. The solution was decanted and diluted with acetone (600 ml) at 18–20° C. Precipitated solid was filtered under N$_2$ and washed with acetone (20 ml). Dried under vacuum at 40–45° C. to get pure Ceftriaxone sodium 25.5 g.

HPLC (purity): 98.0%

Method -II 2-mercapto-5-phenyl-1,3,4-oxadiazolyl-(Z)-4-bromo-2-methoxyimino-3-oxo-butyrate (27.0 g) was taken in mixture of THF (250 ml) and water (125 ml). Thiourea (10.6 g) and sodium acetate (2.0 g) were added to this at 10–15° C. after 45 to 60 min. 7-Amino-3-[[(2, 5-dihydro-6-hydroxy-2-methyl-5-oxo-1,2,4-triazin-3yl)thio]methyl]3-cephem-4-carboxylic acid (20.0 g) was suspended in the reaction mixture. The suspension was stirred for 2–3 hours at a pH of 7.0–8.5 maintained by triethylamine to get clear solution. The reaction mixture was monitored by HPLC. After completion of reaction, 200 ml water was added and pH was adjusted to 7.0. The aqueous layer was separated, charcoalized and treated with sodium-2-ethylhexanoate (30.5 g) in acetone, reaction was proceeded by same method as mentioned in Method -I to get crude ceftriaxone sodium (24.0 g).

Example 4

7-[[(Z)-2-(Aminothiazol-4-yl)-2-methoxyimino] acetamido]-3-methyl-3-cephem-4-carboxylic acid [Cefetamet].

7-Aminodiacetyloxy cephalosporanic acid (2.14 g), active ester, 2-mercapto-5-phenyl-1,3, 4-oxadiazolyl-(Z)-4-bromo-2-methoxyimino-3-oxo-butyrate(3.8 g) were suspended in mixture of THF (20 ml) and water (20 ml). TEA(1.8 g) was added slowly. The reaction was proceeded in same way as described in example II to obtain Cefetamet, 3.25 g.

HPLC (purity): 97.0%

Example 5

7-[[(Z)-2-(Aminothiazol-4-yl)-2-methoxyimino] acetamido]-3-methoxymethyl-3-cephem-4-carboxylic acid [Cefpodoxime acid].

7-Amino-3-methoxymethyl-3-cephem-4-carboxylic acid (24.2 g) and 2-mercapto-5-phenyl-1,3 ,4-oxadiazolyl-(Z)-4-bromo-2-methoxyimino-3-oxo-butyrate (39.7 g) were suspended in 400 ml of THF and water mixture (1:1). At 10° C. TEA added to maintain pH 7–8. The reaction was monitored and proceeded as described in example II (Method-I ). The pH was adjusted to 2.7 using 16–18% sulphuric acid. Solid was cooled to 10°° C., filtered and washed with water (3×50 ml) and finally with acetone (20 ml) to obtain the Cefpodoxime acid, 37.5 g (yield 88%).

HPLC (purity) 98.0%

Example 6

7-[[(Z)-2-(Aminothiazol-4-yl)-2-methoxyimino] acetamido]-3-(furanylcarbonyl) thiomethyl]-3-cephem-4-carboxylic acid (Ceftiofur).

7-Amino-3-[(2-furanylcarboxyl)thiomethyl]-3-cephem-4-carboxylic acid (3.4 g) and 2-mercapto-5-phenyl-1,3,4-oxadiazolyl-(Z)-4-bromo-2-methoxyimino-3-oxo-butyrate were added to a mixture of THF (35 ml) and water (35 ml) at temperature 5° C. The pH of reaction was maintained at 7.5 to 8.5 by addition of TEA during the reaction. After completion of reaction, the reaction was extracted with methylene chloride (25 ml×3). The aqueous layer was diluted with 15 ml THF and thiourea was added to the aqueous and stirring was continued for 30 to 45 min. to complete the cyclisation. After that pH was lowered to 3 by addition of 1N HCl. The solution is saturated by salt. The organic layer was separated and pH was further adjusted to 0.5 by concentrated HCl. IPE (250 ml) was added to precipitate the hydrochloride salt of Ceftiofur, 4.3 g (yield 75.0%).

HPLC (purity): 98.0%

What is claimed is:

1. A novel 2-mercapto-5-phenyl-1,3,4-oxadiazolyl-(Z)-4-bromo-2-methoxyimino butyric acid derivative used in the preparation of cephalosporin antibiotics, and represented by formula (I)

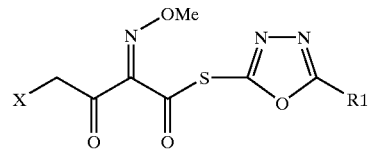

wherein

X represents halogen (Cl, Br and I)

R$_1$ represents C$_1$–C$_4$ alkyl or phenyl.

2. A process for preparing active thioester derivatives represented by formula (I), said process comprises the step of reacting 4-halogeno-2-methoxyimino-3-oxo-butyric acid represented by formula (II)

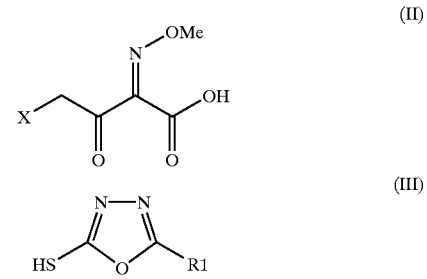

wherein X represents halogen (Cl,Br,I)

wherein R$_1$ represents C$_1$–C$_4$ alkyl or phenyl with thio-oxadiazole of formula (III) in the presence of DMF, phosphorous oxychloride, an organic base and a solvent at temperature being maintained in the range −30° C. to +20° C.

3. A process as claimed in claim 2, wherein the organic solvent is selected from the group comprising dichloromethane, tetrahydrofuran, dioxane, N,N-dimethylformamide, acetonitrile and mixtures thereof.

4. A process as claimed in claim 2, wherein the organic base is selected from the group comprising triethylamine, diethylamine, tributylamine, pyridine, N-alkylanilines, and mixture thereof.

5. A process for preparing a cephalosporin compound of formula (VI)

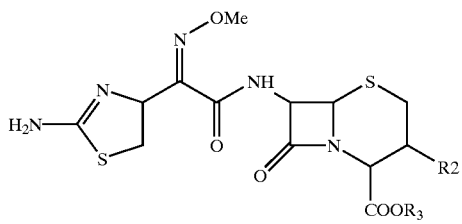

wherein $R_2$ represents H, $CH_3$, $CH_2OCH_3$, $CH_2OCOCH_3$,

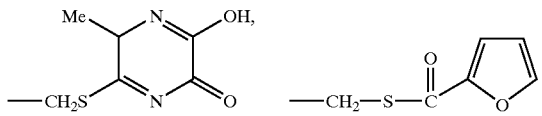

or a standard cephalosporins substituent, $R_3$ is hydrogen, salt or carboxylic protecting group and $R_4$ is hydrogen or silyl, said process comprising the step of reacting a compound of formula (V) with a compound of formula (I) and thiourea

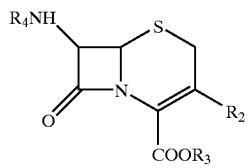

wherein
$R_2$, $R_3$ and $R_4$ are defined as above

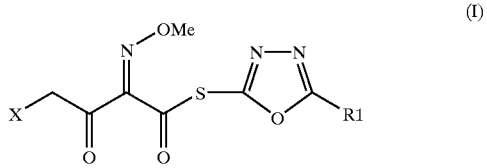

wherein, X & $R_1$ are as defined above.

6. A process for the preparation of cephalosporin compounds of formula (VI) as in claim 5 comprising reacting a compound of formula (I) in a mixture of an organic solvent and water with a compound of formula (V) in the presence of a base at a temperature in the range of 0° C.–30° C. preferably at 15° C., wherein the intermediate which is formed insitu is treated in same reactor with thiourea to obtain compounds of formula (VI).

7. A process for the preparation of cephalosporin compounds of formula (VI) as in claim 5 comprising the step of reacting thiourea with compound of formula (I) in mixture of an organic solvent and water in the presence of base at a temperature in the range of −5° C. to 30° C. preferably at 15° C. followed by the addition of a compound of formula (V) with at pH between 7–8.5 maintained by addition of a base to obtain the cephalosporin compounds of formula (VI).

8. A process as claimed in claim 5, wherein $R_2$ is hydrogen, methyl, methoxymethyl, acetyloxymethyl, (2,5-dihydro-6-hydroxy-2-methyl-5-oxo-1,2,4-triazin-3-yl)thiomethyl, furylcarbonyl thiomethyl or a standard cephalosporin substituent.

9. A process as claimed in claim 5, wherein $R_3$ is or alkali metal salt.

10. A process as claimed in claim 6 or 7, wherein the reaction is effected in the presence of water and an organic solvent selected from the group consisting of tetrahydrofuran, N,N-dimethylacetamide, N,N-dimethylformamide, dioxane, acetonitrile and mixtures thereof.

11. A process as claimed in claim 6 or 7, wherein the reaction is performed in the presence of an organic base selected from the group consisting of triethylamine, N-methylmorpholine, pyridine, N-methylanilines, 1,5-diazabicyclo[4.3.0]non-5-ene, 1,4-diazabicyclo[2.2.2]octane, 4dimethylaminopyridine and mixtures thereof.

12. A process as claimed in claim 6 or 7, wherein said compound of formula (VI) is a syn isomer.

* * * * *

UNITED STATES PATENT AND TRADEMARK OFFICE
CERTIFICATE OF CORRECTION

PATENT NO.   : 6,384,215 B1
DATED        : May 7, 2002
INVENTOR(S)  : Deshpande et al.

It is certified that error appears in the above-identified patent and that said Letters Patent is hereby corrected as shown below:

Column 1,
Line 33, please delete the following formula (IV)

"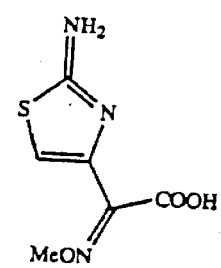"

and replace with the following formula (IV)

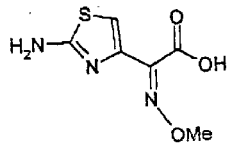

Column 2,
Line 37, delete "PCl₅ Another" and replace with -- PCl₅. Another --.
Line 49, delete "OBJECTS OF THE INVENTION" and replace with -- OBJECTIVE OF THE INVENTION --.

Column 3,
Line 37, delete "obtained quantitative" and replace with -- obtained in quantitative --.

Column 4,
Line 55, delete the following structure:

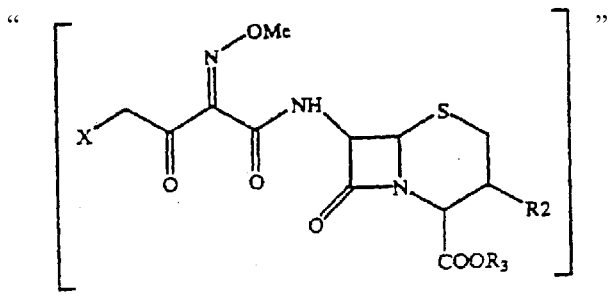

UNITED STATES PATENT AND TRADEMARK OFFICE
CERTIFICATE OF CORRECTION

PATENT NO. : 6,384,215 B1
DATED : May 7, 2002
INVENTOR(S) : Deshpande et al.

It is certified that error appears in the above-identified patent and that said Letters Patent is hereby corrected as shown below:

Column 4, line 55, cont'd,
and insert the following structure:

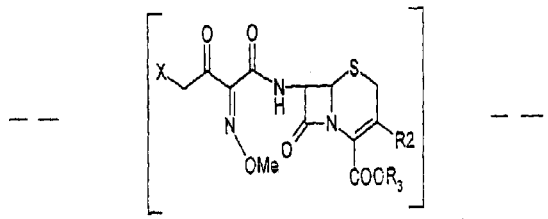

Column 5,
Line 16, delete the following structure:
"

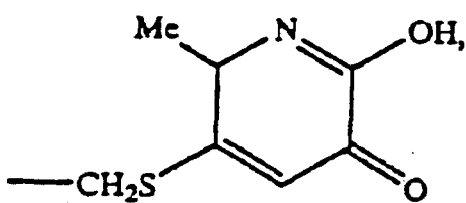

"
and replace with the following structure:

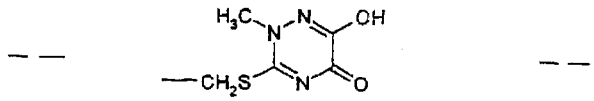

Line 26, delete the word "obtained" and replace with -- obtain --.

Column 7,
Line 1, delete the entire line and replace with -- 2,4-triazin-3-yl)thio]methyl]-3-cephem-4-carboxylic acid --.
Line 5, delete the entire line and replace with -- 2,4-triazin-3-yl)thio]methyl]-3-cephem-4-carboxylic acid --.
Lines 50-51, delete "active ester,".

UNITED STATES PATENT AND TRADEMARK OFFICE
CERTIFICATE OF CORRECTION

PATENT NO. : 6,384,215 B1
DATED : May 7, 2002
INVENTOR(S) : Deshpande et al.

It is certified that error appears in the above-identified patent and that said Letters Patent is hereby corrected as shown below:

Column 8,
Line 11, delete the entire line and replace with -- acetamido]-3-(furanylcarbonyl) thiomethyl]-3-cephem-4- --.
Line 65, delete "wherein $R_1$ represents $C_3$-$C_4$ alkyl or phenyl".
Line 66, delete the entire line and replace with -- oxadiazole of formula (III) wherein R represents $C_3$-$C_4$ alkyl or phenyl in the presence of DMF, --.

Column 9,
Line 15, delete the following structure:

"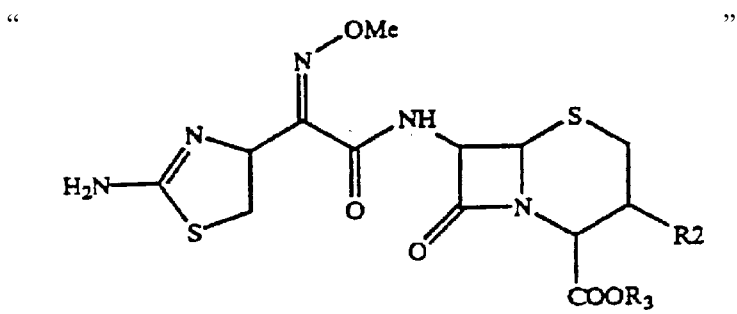"

and insert the following structure:

-- 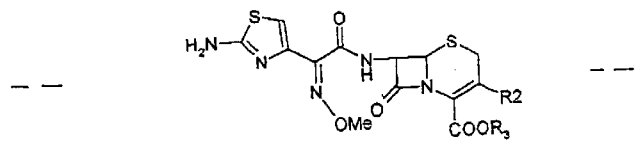 --

UNITED STATES PATENT AND TRADEMARK OFFICE
CERTIFICATE OF CORRECTION

PATENT NO.    : 6,384,215 B1
DATED         : May 7, 2002
INVENTOR(S)   : Deshpande et al.

It is certified that error appears in the above-identified patent and that said Letters Patent is hereby corrected as shown below:

Column 9,
Line 30, delete the following structure:

" 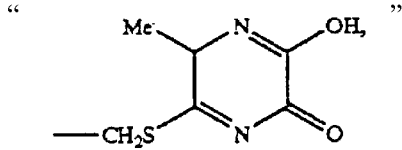 "

and insert the following structure:

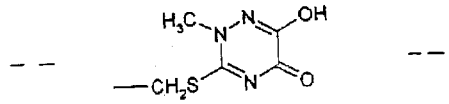

Column 10,
Line 37, delete "N,N-dimethylacetamide".
Line 38, delete the entire line and replace with -- dimethylformamide, dioxane, alcohol and mixtures --.

Signed and Sealed this

Twenty-second Day of July, 2003

JAMES E. ROGAN
*Director of the United States Patent and Trademark Office*